United States Patent [19]
Dunn et al.

[11] Patent Number: 5,897,842
[45] Date of Patent: Apr. 27, 1999

[54] METHOD AND APPARATUS FOR THERMAL CYCLING AND FOR AUTOMATED SAMPLE PREPARATION WITH THERMAL CYCLING

[75] Inventors: James M. Dunn, Scarborough; James Leushner, North York; John Renfrew, Burlington; Paul Waterhouse, Copetown; Alexandre M. Izmailov, Toronto; Henryk Zaleski, Niagara Falls, all of Canada

[73] Assignee: Visible Genetics Inc., Toronto, Canada

[21] Appl. No.: 08/703,730

[22] Filed: Aug. 27, 1996

Related U.S. Application Data

[63] Continuation-in-part of application No. 08/640,672, May 1, 1996, Pat. No. 5,789,168, and application No. 08/684,498, Jun. 19, 1996, Pat. No. 5,830,657.

[51] Int. Cl.[6] .............................. B01L 9/00; C12M 3/02
[52] U.S. Cl. ........................... 422/131; 422/104; 422/64; 422/67; 422/99; 435/286.1
[58] Field of Search ................................ 422/67, 50, 131; 435/283.1, 285.1, 286.1; 165/61

[56] References Cited

U.S. PATENT DOCUMENTS

| | | | |
|---|---|---|---|
| 5,176,203 | 1/1993 | Larzul | 165/61 |
| 5,451,500 | 9/1995 | Stapleton | 435/6 |
| 5,455,175 | 10/1995 | Wittwer et al. | 435/286.1 |
| 5,475,610 | 12/1995 | Atwood et al. | 364/500 |
| 5,578,270 | 11/1996 | Reichler et al. | 422/67 |
| 5,795,547 | 8/1998 | Moser et al. | 422/104 |

FOREIGN PATENT DOCUMENTS

| | | |
|---|---|---|
| 0636413 | 2/1995 | European Pat. Off. . |
| 2650657 | 2/1991 | France . |
| 2672231 | 8/1992 | France . |
| 6030776 | 2/1994 | Japan . |
| 9521382 | 8/1995 | WIPO . |

OTHER PUBLICATIONS

Advertisement for Pharmacia AutoLoad Solid Phase Sequencing Kit.
Brochure for Vistra DNA Labstation 625 (1994).
Advertisement for Qiagen BioRobot 9600.
Brochure for Beckman Biomek 2000 (1994).
Oste, C.C. "PCR Instrumentation: Where Do we Stand", *Polymerase Chain Reaction,* pp. 165–173 (1994).

Primary Examiner—W. Gary Jones
Assistant Examiner—Ethan Whisenant
Attorney, Agent, or Firm—Oppedahl & Larson LLP

[57] ABSTRACT

An apparatus and method for thermally cycling a reaction mixture in a reaction vessel to expose the mixture to the varying temperatures necessary to, for example, achieve PCR amplification or the preparation of sequencing fragments using a cycle sequencing operation makes use of flow-through reaction vessels, such as capillary tubes, for the preparation and thermal cycling of reaction mixtures. In order to prevent loss of the reaction mixture from the vessels during heating, the thermal cycling apparatus of the invention provides means for sealing the proximal and distal end of each reaction vessel. The proximal ends can be sealed by coupling to a pump which permits movement of the samples within the reaction vessels. As to the distal ends, the reaction vessels can be sealed by pressing the distal end of each vessel against a sealing element with a conformable surface, or by immersing the distal end of each vessel in the reservoir of liquid, preferably of an oil, that is not miscible with the reaction mixture.

16 Claims, 4 Drawing Sheets

METHOD AND APPARATUS FOR THERMAL CYCLING AND FOR AUTOMATED SAMPLE PREPARATION WITH THERMAL CYCLING

SPECIFICATION

This application is a continuation-in-part of U.S. patent application Ser. No. 08/640,672 filed May 1, 1996, now U.S. Pat. No. 5,798, 168; and U.S. patent application Ser. No. 08/684,498, filed Jul. 19, 1996, now U.S. Pat. No. 5,830, 657; which are incorporated herein by reference.

BACKGROUND OF THE INVENTION

The present invention relates to a method and apparatus for automating nucleic acid sample preparation.

Sequencing of nucleic acids is generally performed today using the chain termination sequencing method first described by Sanger et al. This process generally involves combining a sample to be analyzed with reagents necessary for synthesis of nucleotide fragments indicative of the sequence of DNA in the sample, i.e, a polymerase enzyme, nucleoside feedstocks and a dideoxynucleoside for chain termination, followed by analysis of the fragments produced by gel electrophoresis. In addition, the sample may be initially amplified, i.e., by polymerase chain reaction (PCR) amplification, to increase the amount of a selected part of the DNA in an original sample prior to performing the sequencing reaction. Thermally stable polymerases, such as Taq Polymerase (Hoffman-La Roche, Inc.) and improved thermal stable chain-termination sequencing enzymes such as Thermo-Sequenase™ (Amersham Life Science, Cleveland) are used to enhance these procedures. These enzymes are utilized in conjunction with multiple successive thermal cycles for amplification or sequencing.

The use of DNA diagnostics in clinical laboratories is not widespread, in part because of the complex and cumbersome steps required to prepare DNA samples for analysis. To overcome this problem, it would be advantageous to have an apparatus which automated the large number of pipetting steps and the thermocycling steps involved in preparing a DNA sample for sequence analysis. At the present time, however, most known robotics have handled either the task of pipetting reagents and sample material to produce a reaction mixture or the task of thermal cycling of the reaction mixture, but not both.

For example, Beckman Instruments, Inc. (Fullerton, Calif.) provides the Biomek® 2000 automated pipetting apparatus, that can automate the sample preparation steps for PCR or DNA sequencing reactions in a 96 well microtiter plate using a group of eight pipetting tips. Trays containing reagents or samples are arranged for sequential liquid transfer functions. Another pipette robot, the QIAGEN BioRobot™ 9600 (QIAGEN Inc., Chatsworth Calif.) can prepare 96 bacterial minipreps in 2 hours. These robots all use a cooling plate to keep the reagents and samples at controlled temperatures (usually 4 degrees C.) during sample preparation.

The reagent trays prepared in an apparatus of this type are then generally transferred to a separate instrument for purposes of thermal cycling. For example, the RoboCycler™ Gradient 96 System (Stratagene, Inc.) has 4 different temperature blocks and a lifter that moves a tray of up to 96 tubes from block to block in sequence. In this way, the apparatus cycles reaction mixtures through a series of temperature increases and decreases as appropriate for amplification or sequencing reactions.

Heating of the temperature blocks in thermal cycling apparatus has been accomplished in a variety of ways, including heating and cooling using liquid flow or electronic means (e.g., resistive heating). An air flow thermal cycling mechanism is made by Idaho Technology (Idaho Falls, Id.). To use this apparatus, capillary tubes containing the desired reaction mixtures are melt-sealed at both ends with a Bunsen burner. The permanently sealed capillaries are inserted through and held in a rubber plug. The plug is placed into an opening in a heat chamber, such that the sealed capillaries are suspended in the heat chamber without touching the walls of the chamber. Air heated to the desired temperature is circulated through the heat chamber, thereby heating and cooling the capillaries as programmed. Upon completion of the desired thermal cycles, the capillaries may be removed from the rubber plug. The capillaries are then broken at both ends, and the reaction mixture is extracted for analysis or for mixing with further reagents. Drawbacks of using this apparatus include that the handling of the capillaries is time consuming and that the procedure requires the use of multiple capillaries for each treatment of the same sample.

While there are many potential advantages to combining sample preparation and thermal cycling into a single apparatus, only one apparatus known to Applicants actually attempts such a combination. The Vistra DNA Labstation 625 (Molecular Dynamics, Sunnyvale Calif.) is a pipette robot that can prepare bacterial mini-preps and PCR and DNA sequencing reactions in a 96 well microtiter plate. The Labstation 625 has an integrated Peltier-block thermocycler for thermal-cycling steps. Using this apparatus, a technician can prepare a sequencing experiment in about 10–15 minutes, and then start the thermocycling procedure. This apparatus uses tubes, and places a layer of oil on top of the reactions to reduce loss of sample during heating. One of the drawbacks of this device, is the long time required for temperature changes due to the use of a heating block.

It is an object of the present invention to provide an improved thermocycler, which can be combined with a sample preparation apparatus if desired.

It is another object of the present invention to provide an apparatus and method for automating the preparation of nucleic acid samples for rapid throughput.

It is a further object to provide a method and apparatus that integrate automation of pipetting functions with thermal cycling to eliminate manual handling and to optimize reaction conditions.

It is further object of the invention to provide a method and apparatus that minimize the risk of contamination between samples and that permit sterility to be maintained throughout the procedure.

It is a further object of the invention to provide an apparatus which is capable of loading prepared nucleic acid samples into an automated DNA sequencing apparatus or onto an electrophoretic analytical gel.

SUMMARY OF THE INVENTION

The present invention provides an apparatus and method for thermally cycling a reaction mixture in a reaction vessel to expose the mixture to the varying temperatures necessary to, for example, achieve PCR amplification or the preparation of sequencing fragments using a cycle sequencing operation. The invention makes use of flow-through reaction vessels, such as capillary tubes, for preparation and thermal cycling of reaction mixtures. In order to prevent loss of the reaction mixture from the vessels during heating, the thermal cycling apparatus of the invention provides means for sealing the proximal and distal end of each reaction vessel. The proximal ends can be sealed by coupling to a pump which permits movement of the samples within the reaction vessels. As to the distal ends, in one embodiment of the invention, the reaction vessels are sealed by pressing the distal end of each vessel against a sealing element with a conformable surface for reversibly sealing the reaction vessels before thermal cycling is begun. This sealing element is suitably a strip of conformable material which provides a plurality of distinct locations against which successive reaction vessels can be pressed, thus reducing the likelihood of contamination between samples. In an alternative embodiment of the invention, the distal end of each vessel is immersed in the reservoir of liquid, preferably of an oil such as mineral oil that is not miscible with the reaction mixture. The head pressure of the liquid acts to hold the reaction mixture within the vessel.

The thermal cycling apparatus of the invention is suitably incorporated as part of an apparatus for performing both sample preparation and thermal cycling. Such an apparatus has a sample preparation region in which sample and reagents are mixed to form one or more reaction mixtures within one or more separate reaction vessels, and a thermal cycling region. A robotic transference element moves the reaction vessels between the sample preparation region and the thermal cycling region, preferably under the control of a microprocessor controller. The apparatus further includes a pump which is used to draw reagents and sample into and out of the reaction vessel within the sample preparation region, thus forming the reaction mixtures within the reaction vessels. The reaction vessels are then transferred to the thermal cycling region for thermal cycling.

DETAILED DESCRIPTION OF THE INVENTION

The present invention provides a novel and improved apparatus for thermal cycling of reaction mixtures such as PCR amplification mixtures or cycle sequencing mixtures. The thermal cycling apparatus of the invention includes a holder for receiving one or more flow-through reaction vessels; means for reversibly sealing the ends of the vessels; and means for controlling the temperature of reaction mixtures within the vessels.

As used herein, the term "reversibly sealing" refers to the formation of a seal at an end of the reaction vessel which can be removed nondestructively and resealed multiple times if necessary without damaging the reaction vessel. Thus, heat sealing the end of a capillary tube and then breaking it open to recover the contents of the tube is not reversible sealing within the scope of the present invention.

The flow-through reaction vessel in which a sample is thermally cycled in accordance with the present invention is hollow and open at both ends. The reaction vessel is typically a capillary tube. The reaction vessel can be made from any non-reactive substance, including glass, non-reactive metals such as stainless steel, non-reactive plastics or composite materials. The capillary tube can also be made as a layered structure with regions of high and regions of low thermal conductivity extending along the axis of the reaction vessel. The inside diameter is preferably about 1.1 mm. Suitable capillaries are Fisherbrand™ or Pyrexbrand™ capillaries sold by Fisher Scientific (Ottawa, Canada).

Figure 1:
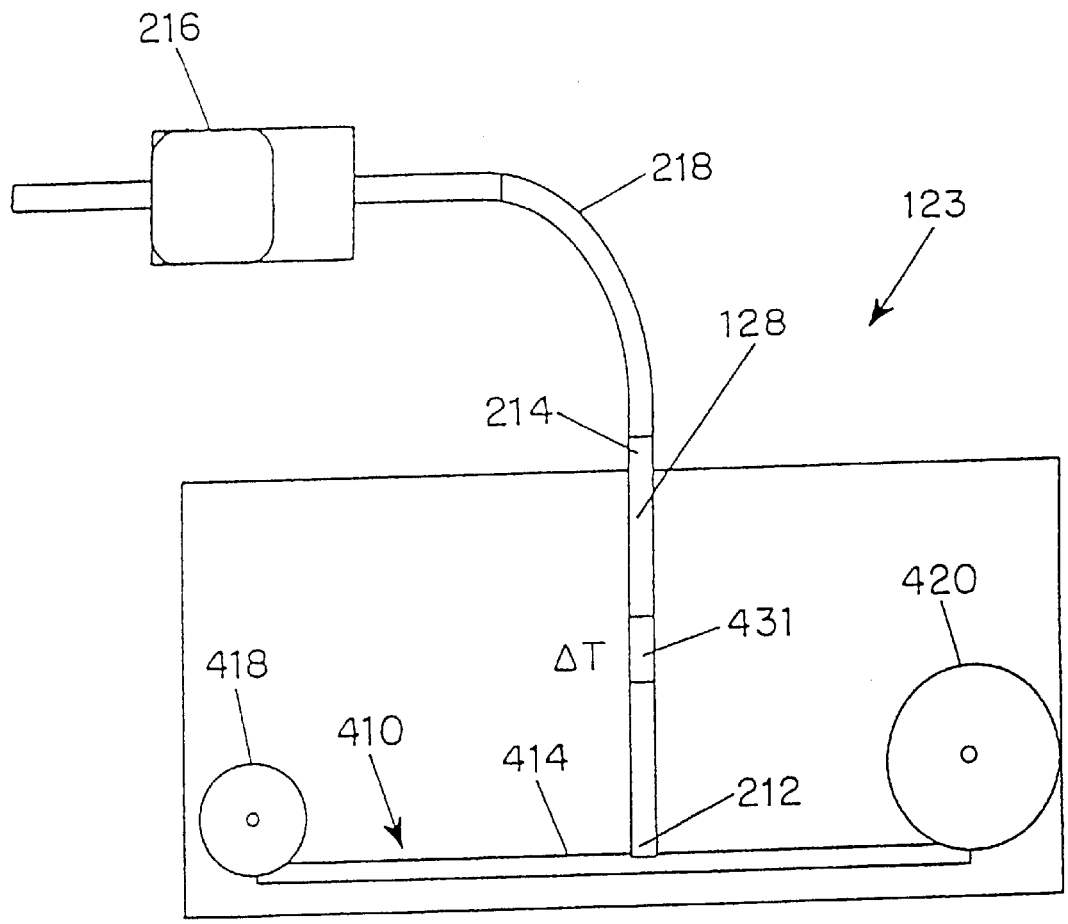
FIG. 1 depicts a side cross-sectional view of a first embodiment of a thermal cycling apparatus having a reversible sealing element in accordance with the invention.

FIG. 1 shows a first embodiment of the thermal cycling apparatus of the invention. As shown, the apparatus includes a thermocycling chamber 123. A flow-through reaction vessel 128 is placed within the chamber 123 for thermal cycling.

Within the thermocycling chamber 123, the distal end 212 of reaction vessel 128 is pressed into contact with a sealing element 410 to reversibly seal the reaction vessel 128 having a reaction mixture 431 therein. Sealing element 410 has a conformable surface 414 against which the distal end 212 of reaction vessel 128 can be placed flush in sealing engagement using a force directed along the axis of the reaction vessel which does do not deflect from this axis in order to limit breakage. Conformable surface 414 is made of a non-reactive elastic substance which must be sufficiently deformable to match the imperfections of distal ends 212, e.g., rubber or neoprene, and is preferably sterile to prevent contamination of contaminant-sensitive samples. Conformable surface 414 may be a strip which forms the surface of sealing element 410 or is the sealing element 410. Sealing element 410 may be wide enough to accommodate 8 to 12 or more reaction vessels, as desired. It is also preferably of small size in order to minimize thermal mass, and is preferably located entirely within thermocycling chamber 123.

During thermocycling, the proximal end 214 of the reaction vessel 128 is also sealed to prevent escape of the reaction mixture. This sealing can be done with a conformable surface comparable to that use to seal the distal ends 212. Preferably, however, the proximal end 214 is sealed by connection to a pump 216, for example via tubing 218. The pump 216 can be used to increase the pressure above the reaction mixture in the reaction vessel 128 after sealing of the distal end 212, thus reducing the amount of solvent lost during the heating steps of the thermal cycling process.

It is understood that a single reaction vessel 128 may be sealed at one time against conformable surface 414. However, it is preferred that multiple reaction vessels 128 be used to increase throughput. Thus, multiple reaction vessels may be present behind reaction vessel 128 along the line of sight.

The apparatus of the invention may include means such as driven rollers 418 and 420 for transporting sealing element 410 within thermocycling chamber 123. Operation of rollers 418 and 420 moves sealing element 410 so that a fresh portion of conformable surface 414 is placed in position for sealing engagement with reaction vessel 128 at the start of each reaction, thus reducing the likelihood of contamination of samples.

In another embodiment, the sealing element may be a cylindrical roll. The cylindrical sealing element is preferably elongated to allow for a plurality of reaction vessels 128 to be sealed against its conformable surface. The cylindrical roll can be rotated after thermal cycling so that a clean portion of its conformable surface is moved into place for contact with distal end 212 of the reaction vessel 128. The cylindrical sealing element may in fact be a cylindrical polygon, have a large number of flat faces to better permit sealing engagement with its conformable surface. A means for transporting this sealing element could be gears to move a member located along the axis of the cylindrical sealing element which protrudes to engage with the gears.

Once the reaction vessel is within the thermocycling chamber 123 and sealed, the temperature within the chamber is varied to cycle the reaction mixture through the sequences of elevated and reduced temperatures desired by the user. Thus, thermocycling chamber 123 is connected to a temperature control device, for example a source of temperature-controlled fluid flow, not shown. Various types of temperature control devices are known in the art, and any can be used in conjunction with the thermocycling chamber of the present invention. See for example, U.S. Pat. No. 5,455,175 to Wittwer et al., which is incorporated herein by reference. For example, in one embodiment of the invention, fluid is circulated by the temperature control device to quickly change the temperature in the thermocycling chamber. The reaction vessels are exposed to the fluid to bring the temperature of the reaction mixture in the vessels to the desired temperature. The reaction mixtures are cycled through a series of temperature increases and decreases according to optimum reaction conditions. It is preferred that the fluid used for thermal transfer be air.

Figure 2A:
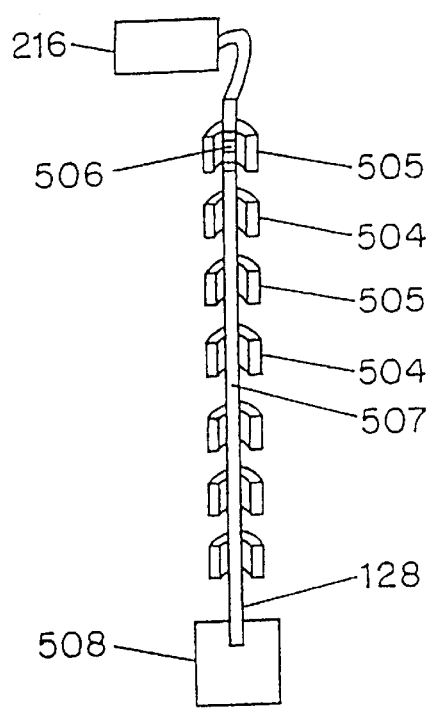
FIGS. 2A and 2B shows a thermal cycling apparatus in accordance with the invention.
Figure 2B:
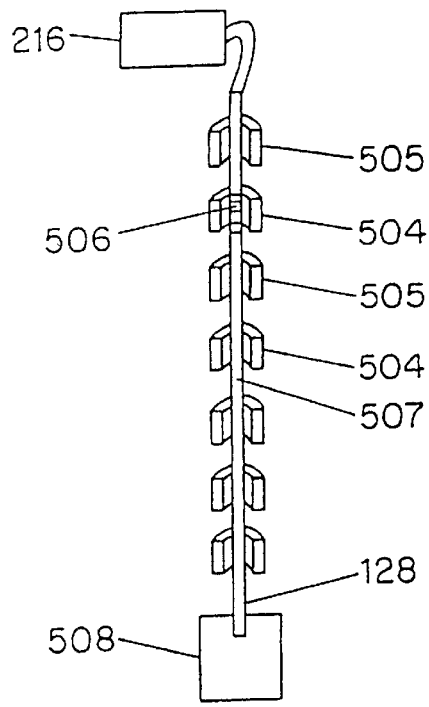

FIGS. 2A and 2B shows a further embodiment of a thermal cycling apparatus in accordance with the invention. In this embodiment, the temperature control device provides a series of temperature regions, each controlled to provide one of the desired temperature regimes of the thermocycle program. Thus, for example, in the embodiment shown in FIGS. 2A and 2B, the temperature control device provides alternating bands of a high denaturation temperature 505 and a lower annealing/extension temperature 504. Temperature regulation can be achieved with resistive heaters and Peltier devices.

In order to achieve thermocycling, the reaction mixture in the reaction vessel is physically moved from one temperature zone to the next. This can be accomplished by shifting the reaction vessel with respect to the temperature control elements, for example by finely adjusted raising and lowering of the reaction vessel using a robotic arm. In the preferred embodiment, shown in FIGS. 2A and 2B, however, the movement of the reaction mixture is accomplished by altering the position of the reaction mixture within the reaction vessel.

Figure 3:
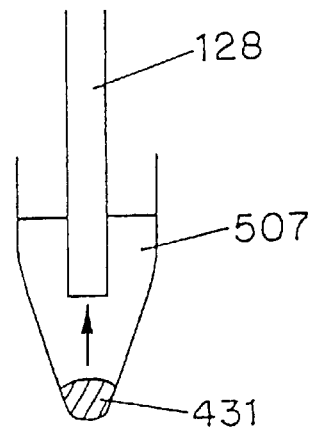
FIG. 3 shows the filling of a reaction vessel for use in a liquid sealed embodiment of the invention.

The proximal end of reaction vessel 128 is connected to a pump 216, and the pump is used to load the reaction vessel with a layer of reaction mixture 506 and a layer of a non-miscible liquid 507 such as an oil. As shown in FIG. 3, this can be accomplished by drawing the reaction mixture into a reaction vessel 128 from a vessel containing the reaction mixture 431 covered with the non-miscible liquid 507.

After filling, the reaction vessel 128 is placed within the apparatus so that the alternating temperature bands 504, 505 extend along the axis of the reaction vessel 128, and the distal end of the reaction vessel is immersed in a reservoir 508 of the non-miscible liquid which serves as a reversible seal for the distal end of the reaction vessel. At the start of the process, the reaction mixture is positioned in alignment with the first high temperature band for denaturation of the material in the mixture as shown in FIG. 2A. After the required period of time at this temperature, the pump 216 is activated to draw the reaction mixture, together with the non-miscible liquid, to the next temperature band for annealing/extension as shown in FIG. 2B. This process is repeated through each of the bands.

Figure 4:
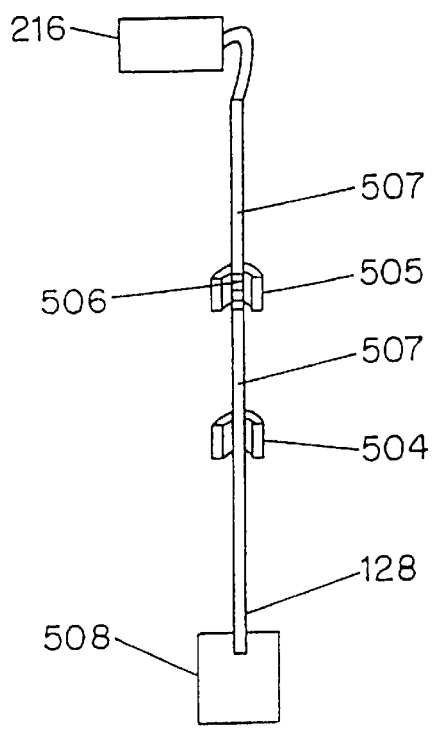
FIG. 4 shows a thermal cycling apparatus in accordance with the invention.

As shown in FIGS. 2A and 2B, the temperature control device can provide multiple bands of each type, up to the number required to perform the desired number of cycles. Preferably, however, the number of temperature control bands will be less than the number required to provide an individual band for each cycle, and indeed may be as few as one temperature control band for each temperature regime to established in the cycling program as shown in FIG. 4. The use of fewer temperature control bands permits greater spacing between the bands, which facilitates maintenance of disparate temperatures in the adjacent regions, and permits a greater versatility.

When there are fewer sets of temperature control bands than the number of cycles to be performed, the pump 216 is used in either a forward or a reverse direction to draw the reaction mixture back and forth through the temperature control bands. The positioning of the reaction mixture relative to the temperature control bands in a thermal cycling apparatus of FIGS. 2A, 2B and 4 can be accomplished through careful regulation of the pump, provided that pump has sufficient sensitivity and fine control. For this purpose, pump 216 is preferably a piston displacement pump with linear actuators. The motor must have sufficient torque to drive the linear actuator, while having sufficient sensitivity to allow precise measurements of very small liquid samples. The Drummond Nanoject™ pump (Cat No. 3-00-203-X, Drummond Scientific Co., Broomall, Pa.) is sensitive to measure nanoliters of fluid.

In addition to relying on the pump, it may be desirable to include a system for monitoring the position of the reaction mixture within the reaction vessel. This monitoring can be done optically, provided that the reaction vessel is transparent. Such monitoring can also be accomplished using a capacitor positioned inside the reaction vessel within each temperature zone which can discriminate between the reaction mixture and the non-miscible fluid, e.g., based on difference in electrical conductivity.

The temperature control bands are suitably arranged to permit intimate contact between the temperature control devices and each individual reaction vessel. Thus, for example, the temperature control bands in the apparatus of the invention can be arranged about one or more cylindrical openings that are just sufficient in size to receive a reaction vessel. Alternatively the temperature control bands may be formed around an elongated rectangular opening that is divided into individual spaces for receiving individual reaction vessels with insulating spacers.

The thermal cycling apparatus of the invention are advantageously combined in a single instrument with a sample preparation apparatus to permit automation of both the pipetting and thermal cycling portions of amplification or sequencing reactions. Such an apparatus has a pipetting region in which samples are prepared and a thermocycling region in which the thermocycling apparatus is disposed. In the pipetting region, robotic mechanisms handle preparation of reaction mixtures within flow-through reaction vessels, which are then transferred in an automated process to and from the thermocycling region. An exemplary apparatus according to this aspect of the invention is shown in FIGS. 5–7.

Figure 5:
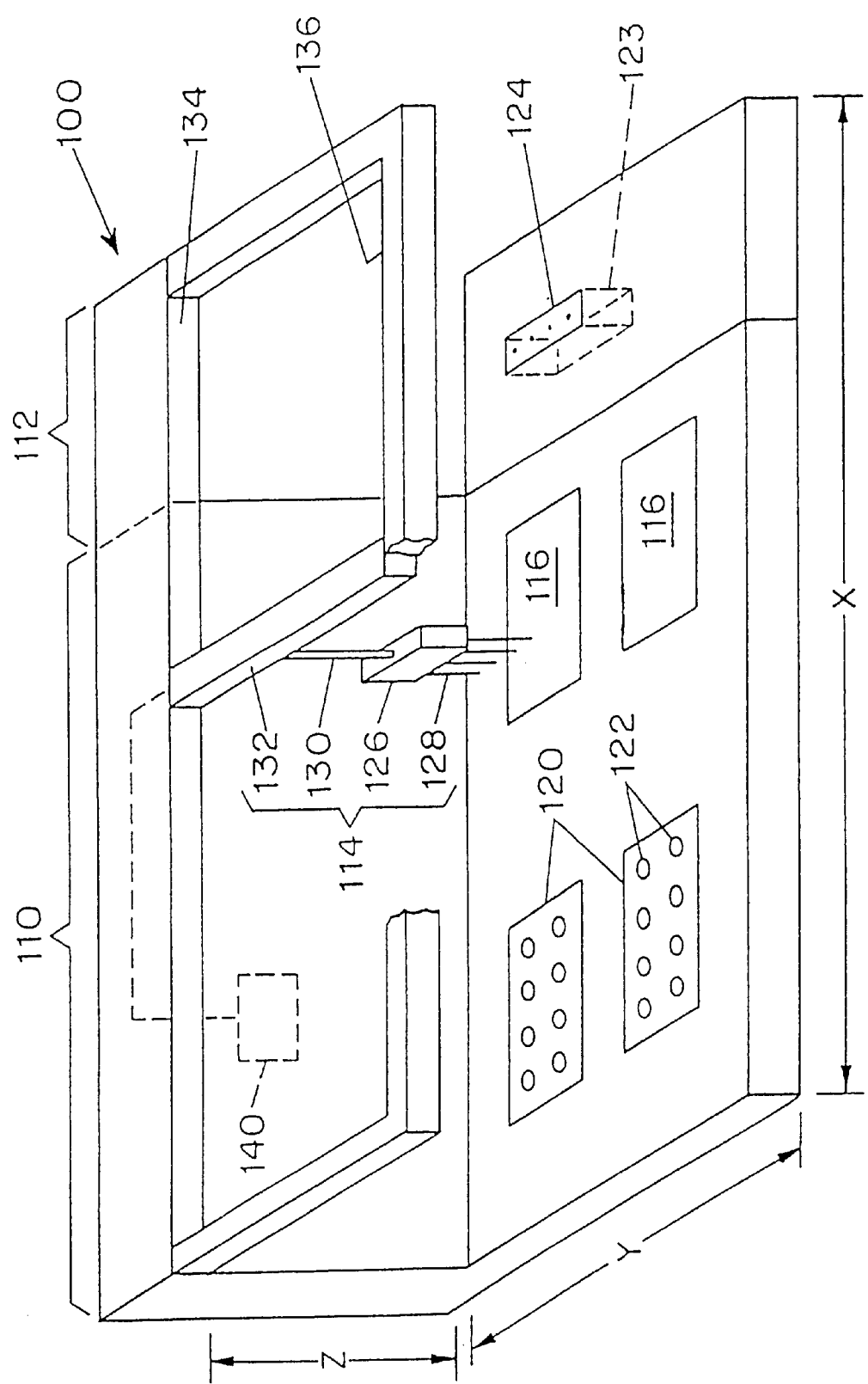
FIG. 5 depicts a robotic apparatus having a pipetting region, a thermal cycling region and a robotic transference element.

FIG. 5 depicts a robotic apparatus 100 having a pipetting region 110, a thermal cycling region 112 and a robotic transference element 114. Robotic apparatus 100 has X, Y and Z displacement axes as shown. Pipetting region 110 has container support members 116 for receiving sample containers such as microtiter plates 120 having wells 122. Container support members 116 are preferably temperature controlled for maintaining the optimum temperature of samples and/or reagents within the sample containers.

Thermal cycling region 112 has a thermocycling chamber 123 accessible to reaction vessels through opening 124.

Figure 6:
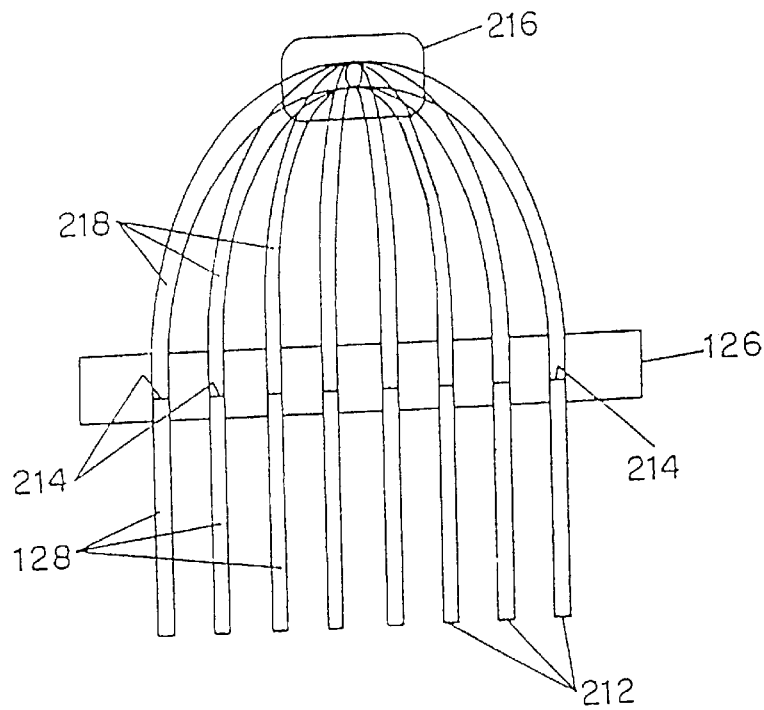
FIG. 6 depicts a plurality of reaction vessels connected to a pump.
Figure 7:
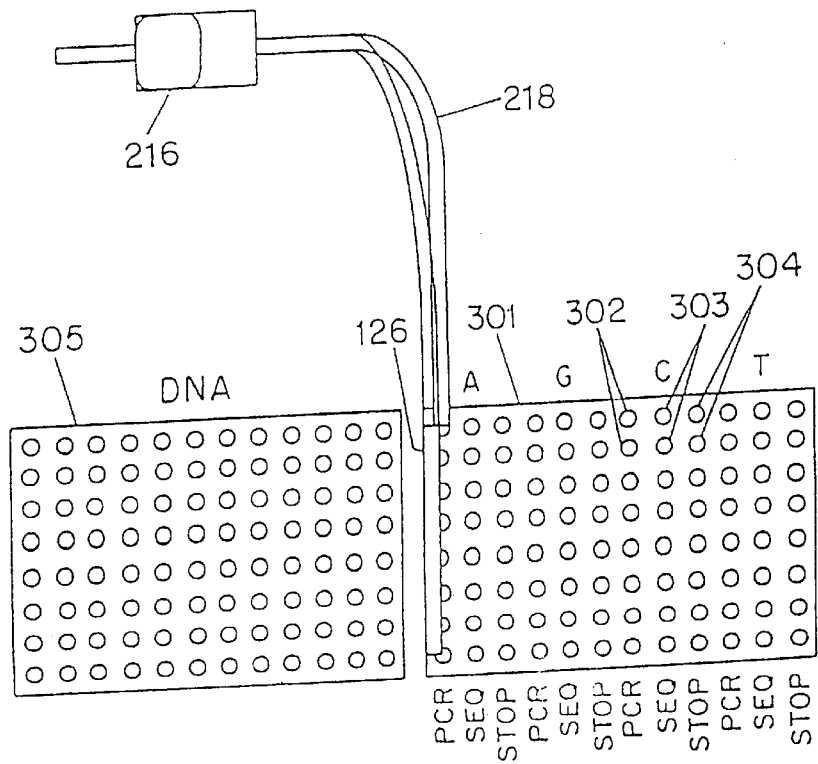
FIG. 7 depicts an example of the placement of samples and reagents in microtiter trays in accordance with an embodiment of the present invention.

Robotic transference element 114 includes reaction vessel holder 126 which can pick up and hold reaction vessels such as reaction vessels 128 which are shown in detail in FIG. 6. Y axis attachment piece 130 suspends reaction vessel holder 126. Y axis attachment piece 130 is movable along the Y axis along the underside of X axis attachment piece 132 so that reaction vessels 128 can access different sample containers located along the Y axis, e.g., either of microtiter plates 120 shown. X axis attachment piece 132 is movable between tracks 134 and 136 and permits reaction vessels 128 to access different sample containers along the X axis and to move between pipetting region 110 and thermal cycling region 112. Once positioned over the desired liquid sample in pipetting region 110, reaction vessels 128 access liquid sample or reagent by movement of the reaction vessel holder 126 downward in the Z direction, for example using a linear carriage driven by a stepper motor. Movement of robotic transference element 114 is determined by a controller 140 which sends signals to robotic transference element 114 to perform various functions in accordance with a program of sample pipetting and transference operations.

In the apparatus of FIGS. 5–7, a plurality of reaction vessels 128, suitably arranged in a parallel array, are used simultaneously to increase sample throughput. As shown in detail in FIG. 6, reaction vessels 128 are held by reaction vessel holder 126. Reaction vessels 128 have distal ends 212 and proximal 214 which are open. Proximal ends 214 are connected to a sensitive two way pump 216, for example by way of tubing 218, to permit withdrawal or expulsion of liquid from reaction vessels 128. As noted above, pump 216 is preferably a piston displacement pump with linear actuators which has sufficient torque to drive the linear actuator, while having sufficient sensitivity to allow precise measurements of very small liquid samples. A single pump may be used for all reaction vessels as shown, or each capillary may have its own dedicated pump.

Wells 122 of a microtiter plate 120 are loaded with reagents for selected thermal cycling reactions, for example: PCR reagents such as primers, nucleotides, buffers, salts and enzyme; DNA sequencing reagents such as primers, nucleotides, buffers, salts and enzyme; and/or stop reagents such as formamide and visible dye, used for inhibiting enzyme action. The initial preparation of a microtiter plate 120 may be performed by the robotic transference element 114 of the apparatus of FIGS. 5–7 or by a commercially available automated sample pipetting instrument. The steps involve sequential pipetting and combining of different reactants. Reagents are typically positioned in a fashion convenient for sequential utilization.

FIG. 7 depicts an example of the placement of samples and reagents in microtiter trays in accordance with an embodiment of the present invention. Reagents for nucleic acid sample preparation are present in microtiter reagent plate 301. A variety of reagents are shown in alternating columns of wells. PCR reagent is present in a column of wells 302. The PCR reagents in the wells generally include all the reaction components required to allow for a PCR reaction of the sample DNA. This may include the following: 1X Taq polymerase Buffer (final: 10 mM Tris-HCl, pH 8.3, 50 mM KCl, 1.5 mM MgCl2, 0.001% gelatin); 8 pMol each primer (one of which may be biotinylated, the other is normal); and 0.2 mM each dNTP 2.5U Taq DNA polymerase. Sequencing reaction mixture is present in a column of wells 303 and stop solution is present in columns of wells 304. The sequencing reaction mixture will include at least a chain terminating nucleoside, and may also include additional sequencing enzyme and feedstocks. Sample microtiter plate 305 is loaded with sample DNA to be tested.

Once the desired reaction mixture is loaded into reaction vessels 128, the reaction vessels 128 are moved in the X direction to above opening 124 in the thermal cycling region.

To use the apparatus of the invention, the necessary samples and reagents are first loaded into containers in pipetting region 110. A fresh capillary 128 or a plurality thereof arrayed in parallel dips into a DNA sample to be tested in the wells of microtiter plate 305. A series of 8 or 12 reaction vessels is most suitable for use with standard microtiter plates. A small volume, for example 0.25 microliters, of DNA from plate 305 is drawn into each capillary 128. Distal ends 212 are moved upward from the sample wells by robotic transference element 114 and are then positioned over reagent plate 301, for example, over the column of PCR reagent wells 302.

From this position, the DNA sample is expelled into wells 302 and fully drawn up and down two or more times to mix the DNA sample and the PCR reagent. Finally, a suitable reaction volume, for example 2 microliters, of reaction mixture is drawn into each reaction vessel 128, the distal ends 212 are removed from the wells and the reaction mixture is drawn up each capillary approximately 2 cm. Robotic transference element 114 then moves each reaction vessel 128 to opening 124 of thermal cycling region 112.

Reaction vessels 128 are lowered into the thermocycling chamber 123 and ends 212 are pressed against a fresh portion of the conformable surface 414 to seal ends 212 of reaction vessels 128. Once sealed, air pressure within the reaction vessels is advantageously increased to a level higher than the vapor pressure of the sample to prevent solution from escaping, especially during the high temperature period of the thermal cycles. This can be done using the pump 216 attached to ends 214. The air pressure can be set at a fixed level and maintained throughout the temperature cycles, or it may be dynamic, varying as the temperature is increased and decreased.

The sealed reaction vessels 128 are then exposed to a programmed series of thermal cycles, generally including at least an annealing/extension phase at a relatively low temperature (i.e, 37 to 72° C.), and a denaturation phase at a relatively high temperature (i.e., 90 to 96° C.). Separate annealing and extension phases may also be used as is well known in the art.

After the appropriate number of thermal cycles, the reaction mixture is brought to room temperature or below and the air pressure inside the capillary is returned to standard. The air-tight seal is broken by separating the ends 212 of the reaction vessels 128 from the conformable surface 414. This is automatically accomplished by robotic transference element 114 moving the reaction vessels away from sealing element 410. The conformable surface remains intact upon breaking the seal with each of the reaction vessels 128.

Reaction vessels 128 are then removed from the thermal cycler by means of the robotic transference element 114.

At this point, the sample may be ready for analysis. If so, then reaction vessels 128 are moved to another column of wells 304 in reagent plate 301 containing stop reagents. The stop reagents may be, for example, dextran blue in formamide. Reaction mixture is expelled from the reaction vessels 128 into the wells 304 and drawn up and down two or more times to mix. This sample should be heat denatured for best results. Two microliters of reaction mixture is drawn into each of the reaction vessels 128, capillary ends 212 are removed from the wells 304 and the mixture is drawn up each of the reaction vessels 2 cm. The robotic transference element 114 then moves the reaction vessels 128 back into the thermal cycling chamber 123. Reaction vessels 128 are again sealed against the conformable surface 414. Pressure from the pump is increased. The reaction mixtures are then subjected to circulating air at 90° C. to denature the sample.

More commonly, however, sample preparation will not be complete after only one set of thermal cycles, but will require the addition of further reagents and a further set of thermal cycles, for example for sequencing. In this case, after the initial reactions, rather than proceeding to the stop solution wells 304, the ends 212 of reaction vessels 128 are placed in the sequencing reaction mixture in wells 303. Each sequencing reaction mixture contains one species of chain terminating dideoxynucleotide (either ddATP; ddCTP; ddGTP or ddTTP), and may contain other reaction components such as: Thermo Sequenase™ buffer (final: 26 mM Tris-HCl, pH 9.5, 6.5 mM $MgCl_2$); ~30 ng/5 pM Fluoresceinated sequencing primer; distilled water; Thermo Sequenase™ enzyme; plus desired amounts of dNTPs.

The products of the initial thermal cycling reactions are thoroughly mixed by successive drawing and expulsion from the reaction vessels 128. Finally, a suitable reaction volume, for example 2 microliters, is drawn into capillary 128; the capillary ends 212 are removed from the wells and the samples are drawn about 2 cm up into the capillary. The reaction vessels 128 are transferred to thermal cycling region 112 and lowered into the thermal cycling chamber 123. The ends 212 are pressed into the conformable surface 414. Air pressure is again increased inside reaction vessels 128 to prevent evaporation of sample, and the second round of thermal cycling then is carried out. A suitable regime for thermal cycling in a sequencing reaction is: heat to 94° C. for 2 minutes 25 cycles of 94° C. for 30 seconds;

50° C. for 10 seconds;

70° C. for 30 seconds; and finish at 70° C. for 2 minutes, although persons skilled in the art will understand that these temperatures and times, as well as the number of cycles, depend on the specific material being sequenced and the enzyme being employed.

After the appropriate number of thermal cycles, the samples are returned to room temperature or below and the air pressure inside reaction vessels 128 is returned to ambient. The reaction vessels are then removed from the thermal cycler. The conformable surface 414 advances so that a fresh section is in place. At this point the sample may be mixed with stop solution, as described above, or further reactions may be performed.

Once sample preparation is completed, the robotic transference element 114 may load the samples directly into a sample analyzing instrument, such as an automated DNA sequencing apparatus or into an electrophoresis analytical system. The robotic arm aligns to the loading site and expels the denatured reaction products into the loading site.

The method and apparatus of the present invention are well-suited to performing cycle sequencing reactions and amplification reactions, and in particular to carrying out a number of successive reactions on the same sample in which the same reaction vessel can be used throughout. For example, the processes of amplifying and sequencing nucleic acid samples for clinical analysis may progress automatically in the same reaction chamber in accordance with the present invention after initial setup and programming. The method and apparatus of the invention are also well-suited for single-tube/single-reaction preparation of DNA sequencing fragments as described in U.S. patent application Ser. No. 08/640,672, and U.S. patent application Ser. No. 684,498, filed Jul. 19, 1996.

What is claimed is:

1. An apparatus for thermocycling a reaction mixture contained within a hollow tubular reaction vessel having open proximal and distal ends, comprising:

(a) a housing for receiving a hollow tubular reaction vessel;

(b) means for reversibly sealing the distal end of the hollow tubular reaction vessel received within the housing;

(c) means for reversibly sealing the proximal end of the hollow tubular reaction vessel received within the housing; and (d) means for controlling the temperature of a reaction mixture within the hollow tubular reaction vessel received within the housing, wherein the means for reversibly sealing the distal end of the hollow tubular reaction vessel received within the housing comprises a sealing element disposed within the housing and having a conformable surface which forms a seal with the distal end of the reaction vessel when the distal end of the reaction vessel is pressed into contact with the conformable surface, further comprising means for transporting the sealing element to provide a clean portion thereof for contact with reaction vessels during successive uses of the apparatus.

2. The apparatus according to claim 1, wherein the means for transporting the sealing element comprises a driven roller.

3. The apparatus according to claim 1, wherein the conformable surface is a strip which remains intact upon breaking the seal with each of the reaction vessels.

4. An apparatus for thermocycling a reaction mixture contained within a hollow tubular reaction vessel having open proximal and distal ends, comprising:

(a) a housing for receiving a hollow tubular reaction vessel;

(b) means for reversibly sealing the distal end of the hollow tubular reaction vessel received within the housing;

(c) means for reversibly sealing the proximal end of the hollow tubular reaction vessel received within the housing; and (d) means for controlling the temperature of a reaction mixture within the hollow tubular reaction vessel received within the housing, wherein the means for reversibly sealing the distal end of the hollow tubular reaction vessel received within the housing comprises a reservoir filled with a liquid which is not miscible with the reaction mixture disposed in the reaction vessel.

5. The apparatus according to claim 4, wherein the liquid is an oil.

6. The apparatus according to claim 4, wherein the means for controlling the temperature of a reaction mixture within the hollow tubular reaction vessel received within the housing comprises a plurality of temperature control elements arranged in a linear array extending parallel to the axis of the reaction vessel disposed in the housing, said temperature control elements providing regions of at least two distinct temperatures within the reaction vessel; and means for moving a reaction mixture in a reaction vessel disposed within the housing relative to the temperature control elements, whereby the reaction mixture is exposed to thermal cycling.

7. The apparatus according to claim 6, wherein the means for sealing the proximal end of a reaction vessel disposed within the housing is a pump, and wherein said pump also functions as the means for moving a reaction mixture relative to the temperature control elements.

8. An apparatus for forming a reaction mixture from each of a plurality of liquid samples in each of a corresponding plurality of hollow tubular reaction vessels having open proximal and distal ends and exposing the reaction mixture in the reaction vessels to a predetermined program of temperature variations, comprising:

(a) a pipetting region comprising one or more supports for holding one or more containers of liquid samples and reagents;

(b) a pump operatively connectable to the proximal end of each of the reaction vessels for moving a liquid sample into and out of each of the reaction vessels;

(c) a thermal cycling region comprising a thermocycling apparatus, said thermocycling apparatus comprising
a housing for receiving a hollow tubular reaction vessel;
means for reversibly sealing the distal end of the hollow tubular reaction vessel received within the housing;
means for reversibly sealing the proximal end of the hollow tubular reaction vessel received within the housing; and
means for controlling the temperature of a reaction mixture within the hollow tubular reaction vessel received within the housing; and (d) a robotic transference element for moving each of the reaction vessels having a reaction mixture therein from the pipetting region to the thermal cycling region and placing the distal ends of the reactions vessels into sealing contact with the means for reversibly sealing said distal ends, and for moving each of the reaction vessels from the thermal cycling region to the pipetting region.

9. The apparatus according to claim 8, wherein the means for reversibly sealing the distal end of the hollow tubular reaction vessel received within the housing comprises a sealing element disposed within the housing and having a conformable surface which forms an air-tight seal with the distal open end of each of the reaction vessels when the distal open end of each of the reaction vessels is pressed into contact with the conformable surface.

10. The apparatus according to claim 9, further comprising means for transporting the sealing element to provide a clean portion thereof for contact with reaction vessels during successive uses of the apparatus.

11. The apparatus according to claim 10, wherein the means for transporting the sealing element comprises a driven roller.

12. The apparatus according to claim 9, wherein the conformable surface is a strip which remains intact upon breaking the seal with each of the reaction vessels.

13. The apparatus according to claim 8, wherein the means for reversibly sealing the distal end of the hollow tubular reaction vessel received within the housing comprises a reservoir filled with a liquid which is not miscible with the reaction mixture disposed in the reaction vessel.

14. The apparatus according to claim 13, wherein the liquid is an oil.

15. The apparatus according to claim 13, wherein the means for controlling the temperature of a reaction mixture within the hollow tubular reaction vessel received within the housing comprises a plurality of temperature control elements arranged in a linear array extending parallel to the axis of the reaction vessel disposed in the housing, said temperature control elements providing regions of at least two distinct temperatures within the reaction vessel; and means for moving a reaction mixture in a reaction vessel disposed within the housing relative to the temperature control elements, whereby the reaction mixture is exposed to thermal cycling.

16. The apparatus according to claim 15, wherein the means for sealing the proximal end of a reaction vessel disposed within the housing is a pump, and wherein said pump also functions as the means for moving a reaction mixture relative to the temperature control elements.

\* \* \* \* \*